United States Patent [19]

Feldman

[11] 4,167,283
[45] Sep. 11, 1979

[54] APPARATUS FOR APPLYING A SOFT CONTACT LENS

[76] Inventor: Michael A. Feldman, 864 Glenridge Ave., North Woodmere, N.Y. 11581

[21] Appl. No.: 892,930

[22] Filed: Apr. 3, 1978

Related U.S. Application Data

[63] Continuation-in-part of Ser. No. 818,400, Jul. 25, 1977, abandoned.

[51] Int. Cl.² .............................................. A61F 9/00
[52] U.S. Cl. .................................... 294/1 CA; 294/25
[58] Field of Search .................... 294/1 CA, 25, 64 R; 2/21; 224/28 F

[56] References Cited

U.S. PATENT DOCUMENTS

| 450,447 | 4/1891 | Buchwalter | 294/25 |
| 1,316,436 | 9/1919 | Feeney | 294/25 |
| 3,031,918 | 5/1962 | Moyers | 294/1 CA X |
| 3,132,887 | 5/1964 | Martinez | 294/1 CA X |
| 3,139,298 | 6/1964 | Grabiel | 294/1 CA |
| 3,177,874 | 4/1965 | Spriggs | 294/1 CA UX |
| 3,490,806 | 1/1970 | Lopez-Calleja et al. | 294/1 CA |
| 3,879,076 | 4/1975 | Barnett | 294/1 CA |
| 4,026,591 | 5/1977 | Cleaveland | 294/1 CA |

FOREIGN PATENT DOCUMENTS 31571 9/1900 Austria ........................................ 294/25

Primary Examiner—Johnny D. Cherry
Attorney, Agent, or Firm—Peter L. Berger

[57] ABSTRACT

Apparatus for applying a soft contact lens to the surface of an eye is disclosed to include a thimble section, a cup section and a stem section therebetween. The soft contact lens is retained on the cup section by capillary attraction during placement. The diameter of the cup section is less than the diameter of the lens being placed in order to cause the capillary attraction between the cup section and lens section to be less than the capillary attraction between the lens and the surface of the eye thereby permitting sure and easy placement.

12 Claims, 3 Drawing Figures

4,167,283

APPARATUS FOR APPLYING A SOFT CONTACT LENS

CROSS-REFERENCES TO RELATED APPLICATIONS

This application is a continuation-in-part of application Ser. No. 818,400, filed July 25, 1977, now abandoned.

BACKGROUND OF THE INVENTION

1. Field of the Invention

This invention relates generally to improvements in contact lens applicators, and more particularly to an applicator for applying a soft contact lens to the surface of the human eye.

2. Description of the Prior Art

Contact lens applicators are generally known. The early applicators were designed primarily for the application of rigid contact lenses. Such known devices have included holders, suction apparatus, springloaded devices, lighting devices and eyepieces. Additionally, there have been structures which are specifically designed for soft lens application and removal. (U.S. Pat. No. 3,879,076).

The prior art devices may be described generally as comprising manipulation means for establishing a suction between the lens and the applicator means for holding the lens in a desired position during application or removal. Such devices, however, have involved suction created means, moving parts and other relatively complex expensive components. Additionally, the lens supporting means is rigid which is undesirable for use with the soft contact lens as hereinafter set forth. Further, such devices are relatively difficult to use by less dextrous individuals, for example the typical post-cataract patient who ordinarily is a person of advanced age. Known devices require the full use of one and often both hands of the user, thus making difficult or impossible manipulation of the user's eyelid or eyelids, if necessary.

This invention allows both hands to be free for manipulation of upper and lower eyelids if necessary. It also provides for a finger attachment which allows the lens to be placed in a position which is most desirable, namely the ball of the index finger.

There are also devices, such as the Luma-Serter Attachment manufactured by the DMV Contact Lens Company which include a soft concave cup for holding a contact lens to be inserted. The attachment is adapted to be attached to a penlight and the concave cup is manipulated by the concurrent use of the user's finger and thumbs. Similarly, there are hard contact lens removers formed of a thin-tubular member adapted to be held between the finger and thumb, to be placed on the contact lens creating enough suction to remove the lens from the eye.

Neither of these devices operate as an extension of the user's finger but require more than one finger to control. The present inserter is controlled by one finger and is constructed to operate as though it were part of the finger, with the contact lens support member extending from the body of the inserter in the same general direction as the finger moves when inserting the contact lens.

SUMMARY OF THE INVENTION

It is an object of the present invention to provide an applicator for a soft contact lens which is simple in construction and without moving parts.

Another object of the present invention is to provide an applicator for a soft contact lens which permits release of the lens to the eye surface immediately upon contact with the eye including a relatively resilient lens supporting cup and cup-supporting structure whereby the soft lens can be shaped to the contour of the anterior surface of the cornea or sclera without damage to lens or eye in order to express most of the air bubbles from beneath the lens thereby significantly reducing the chance of the lens wrinkling or disengaging the eye on blinking.

A further object of the present invention is to provide an applicator for a soft contact lens which allows use of both hands to manipulate the upper and lower eyelids of the user, if necessary.

These objects and others not enumerated are achieved by a lens applicator according to the invention, one embodiment of which may include a thimble section to accommodate the insertion therein of the finger tip of a user, a cup section to accommodate the retention thereon of a lens to be applied, a stem section rigidly secured at one end to the thimble section and at its other end to the cup section and a passageway providing air communication from the cup section through to the cavity of the thimble section, the passageway including throughbores in the cup section and a wall of the thimble section and a longitudinally extending passage extending through the stem section.

Another embodiment of this invention may include all of the above except that the stem may be solid and air communication may be provided for by throughbores in the periphery of the cup section.

A lens applicator structured accordingly has been found to become, effectively, an extension of the user's finger which holds the soft contact lens securely exclusively by means of capillary attraction.

BRIEF DESCRIPTION OF THE DRAWINGS

A more complete understanding of the present invention may be had from the following detailed description of a preferred embodiment thereof particularly when read in the light of the accompanying drawings, wherein.

DETAILED DESCRIPTION OF THE PREFERRED EMBODIMENT

Figure 1:
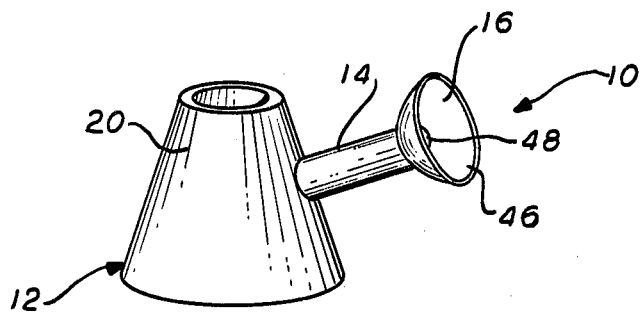
FIG. 1 perspective view of lens applicator according to the present invention.

As stated above, the present invention relates to apparatus for applying a soft contact lens to the surface of an eye. A preferred embodiment of apparatus according to the invention is shown in FIG. 1 and designated generally by the reference numeral 10.

Apparatus 10 includes three basic sections, a thimble section designated generally by the reference numeral 12, a stem designated generally by the reference numeral 14 and a cup section designated generally by the reference numeral 16.

Figure 2:
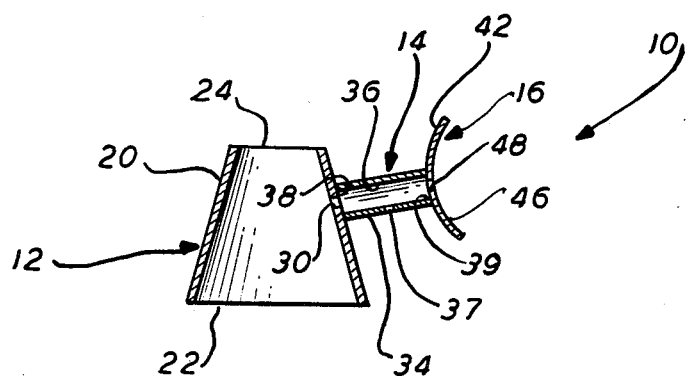
FIG. 2 is a cross-sectional elevational view of the apparatus shown in FIG. 1.

As can be seen with reference to FIGS. 1 and 2, thimble section 12 is a frusto-conical element, having a generally conically shaped outer wall 20. The conical form of wall 20 defines a larger diameter open end 22 and a relatively smaller diameter end opening 24. The thimble section 12 may be a single integral structure formed of suitable material such as rubber or a deformable resilient plastic which may be selected from any of the many plastics known generally in these arts. The shape may be defined by a molding or drawing process, both of which are well known.

Formed in wall 20 of thimble section 12 is a throughbore 30 (FIG. 2). Throughbore 30 places the interior of thimble section 12 in air communication with the interior of stem section 14.

More specifically, stem section 14 comprises a generally tubular member 34 having a longitudinally extending bore 36 formed therethrough. Bore 36 defines a first opening 38 in stem 14 and a second opening 39 in stem 14. An opening 37 is formed in the wall of tubular member 34 to permit free passage of air into or out of bore 36. The stem section 14, at its end having first opening 38 is secured to the outer surface of wall 20 of thimble section 12 in such a position as to cause bore 36 of stem section 14 to be in air communication with throughbore 30 formed in wall 20. The longitudinal axis of stem section 14 may be normal to the taper of thimble section 12 or, more desirably may be mounted at a slight upward angle to facilitate use in placing a lens.

Secured to stem section 14 at its end having a second opening 39 is cup section 16. Cup section 16 is a generally concave-convex member having a convex surface 42 and a concave surface 46. The convex surface 42 of cup section 16 is secured to stem section 14. Further there is formed through cup section 16 a throughbore 48 which throughbore is in air communication with bore 36 of stem section 14. Thus, throughbores 48 and 30 cooperate with bore 36 of stem section 14 to define an air passage from the cavity of thimble section 12 to the cup section 16.

As will be recognized by those skilled in these arts the stem section 14 and cup section 16 may be manufactured from any of a plurality of suitable nontoxic rubber or plastic materials. Typically stem section 14 may be formed by extruding or molding and cup section 16 may be formed by molding or like processes.

Nevertheless, the cup section 16 must be sufficiently resilient to permit deformation upon application to the eye without damage to the eye or the contact lens. Additionally, the cup section must be sufficiently resilient to deform the lens without injury to the eye to express bubbles from between the lens and the anterior surface of the cornea or sclera to significantly reduce the likelihood of lens wrinkling or disengagement upon blinking the eye.

Similarly, the intersection of the stem section 14 with the cup section 16 and preferably the entire stem section should be sufficiently resilient to permit deflection during insertion to prevent injury to the eye or damage to the lens.

It has also been found that there is a significant dimensional relationship between the lens and the concave surface 46 of the cup section 16. The lens, when seated on the concave surface in general conformity therewith should not extend beyond the rim thereof more than approximately 1.0 mm otherwise there is a tendency for the lens to invert its concavity during insertion, a condition frequently experienced when insertion is made by applying the lens on the end of the finger. Therefore, due to the fact that soft contact lenses are made in various diameters, the preferred embodiment may have cup sections of various diameters to insure this geometric ratio. The lens should not fall inside of the periphery of the cup section 16 either.

Considering now the use of lens applicator 10, the index finger is inserted into the cavity of thimble section 12 through open end 22. The hand of the user is held such that the stem section 14 and therewith cup section 16 extend generally upwardly. Both cup section 16 and a contact lens to be applied are wetted and the contact lens is positioned on cup section 16 with the convex surface of the contact lens extending into the concave portion of the cup section.

With the lens in such a position it is retained in cup section 16 through the capillary attraction between the lens and the cup section. No suction is involved. In fact, in order for the contact lens to disengage from the applicator without having the cup section of the invention adhering to the eye, suction must be absent.

The finger of the user having the device 10 thereon may now be moved to the eye such as to cause engagement of the concave interior surface of the lens with the surface of the eye. Because the diameter of cup section 16 is less than the diameter of the lens, the capillary attraction between the concave surface of the lens and the surface of the eye is greater than that between the cup section 16 and the lens. Thus, with the lens positioned, the apparatus 10 may be removed from the lens without withdrawing the lens. In this regard, no suction between lens and cup section is created by reason of the airway established by the cooperation of throughbores 30 and 48 with bore 36.

In actual practice a device 10 according to the present invention has been found to be satisfactory if structured such that the exterior of the thimble section tapers from a diameter of 21 mm to a diameter of 15.0 mm. The wall thickness of the thimble section may be 1.5 mm at the base and 2.5 mm at the apex. Depending upon the size of the lens to be applied, the diameter of cup section 16 may range between 12 and 14 mm. Throughbore 48 in the cup may be 2.5 mm. The stem section may be approximately 8 mm long and 6 mm in diameter. Bore 36 therethrough may be any suitable diameter but not so large as to render the stem section flaccid.

Figure 3:
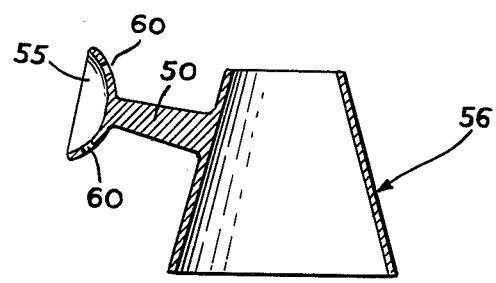
FIG. 3 is a cross-sectional elevational view of an alternative embodiment.

Yet another embodiment of the present invention in shown in FIG. 3. The only difference between FIGS. 2 and 3 is that stem 50 is a solid deformable stem and replaces the hollow stem 14 shown in FIG. 2. Thus, there is no air communication between cup section 55 and thimble section 56. Rather, the elements of FIG. 3 which perform the function of creating an absence of suction are throughbores 60 arranged near the periphery of cup section 55. Indeed, only one throughbore 60 is required to prevent suction. Those skilled in the art will realize that the embodiment disclosed in FIG. 3 will perform substantially identically to the embodiment disclosed in FIG. 2 with the exception that stem 50, being solid, may not be as flexible as stem 14. This fact is not deemed critical and if necessary may be compensated for by manufacturing stem 50 from material having greater resiliency than that of the material utilized to manufacture stem 14.

It will be recognized by those skilled in these arts that the applicator of the present invention embodies a simple, inexpensive and easy to use device. It will also be recognized that various modifications may be made to the preferred embodiment without departing from the spirit and scope of the invention.

I claim:

1. A contact lens inserter for soft contact lenses for applying said soft contact lens to the surface of an eye comprising:
    a finger receiving means comprising a flexible material having a tapered wall construction for snugly receiving a fingertip therein so that the fingertip controls the movement of said inserter,
    a lens support member comprising a generally concave cup for holding said lens,
    an opening formed in said lens support member to preclude creation of suction therein which would tend to hold said contact lens in said lens support member,
    and a stem member connecting said lens support member to said finger receiving means, said stem member extending substantially orthogonally with respect to the ball of the finger and substantally laterally with respect to the axis of the finger, so that said lens support member approaches the eye in the same direction as the ball of the finger approaches the eye.

2. A contact lens inserter as claimed in claim 1, wherein said concave cup has a diameter which is smaller than the diameter of said soft contact lens.

3. A contact lens inserter as claimed in claim 2, wherein the diameter of said lens support member is smaller than the diameter of said soft contact lens by no greater than two millimeters.

4. A contact lens inserter as claimed in claim 2, wherein said lens support member is sized in relationship to said lens to add peripheral support to said contact lens to prevent inversion of said lens.

5. A contact lens inserter as claimed in claims 1 or 2, wherein said concave cup comprises a rubber material.

6. A contact lens inserter as claimed in claims 1 or 2, wherein said finger receiving means, said stem member and said lens support member are formed of a rubbery type material.

7. A contact lens inserter as claimed in claim 1, wherein said stem member comprises a tubular construction having a longitudinal opening therethrough, said opening formed in said lens support member being in air communication with said longitudinal opening to preclude creation of said suction.

8. A contact lens inserter as claimed in claim 7, wherein said finger receiving means comprises an opening which is in air communication with said opening in said lens support member through said longitudinal opening.

9. A contact lens inserter as claimed in claim 7, wherein said stem member comprises an aperture in air communication with said longitudinal opening to preclude said suction.

10. A contact lens inserter as claimed in claim 1, wherein said tapered wall construction of said finger receiving means comprises a frusto-conical member.

11. A contact lens inserter as claimed in claim 1, wherein said lens support member is sufficiently resilient to distort the lens on application to express bubbles from between the lens and the surface of the eye without damage to the lens or injury to the eye.

12. A contact lens inserter as claimed in claim 1, in which the juncture between the stem member and the lens support member is sufficiently resilient to permit deflection of the lens support member upon application of the lens to the eye to ensure secure continuous, surface-to-surface contact between the lens and the surface of the eye without injury to the eye or damage to the lens.

* * * * *